US005489258A

United States Patent [19]

Wohnsen et al.

[11] Patent Number: 5,489,258

[45] Date of Patent: Feb. 6, 1996

[54] MULTI-POSITION BODY SUPPORT

[75] Inventors: Kristine F. Wohnsen; Sam J. Camardello, both of Dolgeville; Elsie M. Bussey, Bay Shore Long Island, all of N.Y.

[73] Assignee: Bissell Inc., Grand Rapids, Mich.

[21] Appl. No.: 62,069

[22] Filed: May 14, 1993

[51] Int. Cl.$^{6}$ .......... A61F 5/00

[52] U.S. Cl. .......... 602/5; 280/250.1; 297/DIG. 10; 606/244; 5/86.1; 5/610

[58] Field of Search .......... 5/81.1, 86.1, 610, 5/650, 651; 280/250.1; 297/DIG. 10; 482/66, 68; 606/241, 243, 244; 602/5; 128/871

[56] References Cited

U.S. PATENT DOCUMENTS

| | | | |
|---|---|---|---|
| 2,210,269 | 8/1940 | Taylor . | |
| 3,249,368 | 5/1966 | Ginzburg . | |
| 3,854,157 | 12/1974 | Trimble . | |
| 3,958,568 | 5/1976 | Gaddy . | |
| 3,971,587 | 7/1976 | Curtis et al. . | |
| 4,029,089 | 6/1977 | Mulholland | 602/5 |
| 4,161,946 | 7/1979 | Zuesse . | |
| 4,456,086 | 6/1984 | Wier et al. | 297/DIG. 10 X |
| 4,470,857 | 9/1984 | Casalon . | |
| 4,620,714 | 11/1986 | Davis | 482/68 X |
| 4,623,194 | 11/1986 | Pillot | 297/DIG. 10 X |
| 4,809,804 | 3/1989 | Houston et al. | 297/DIG. 10 X |
| 4,968,050 | 11/1990 | Kendrick et al. | 297/DIG. 10 X |
| 4,987,622 | 1/1991 | Shockey | 5/610 X |

*Primary Examiner*—Linda C. Dvorak
*Attorney, Agent, or Firm*—Varnum, Riddering, Schmidt & Howlett

[57] ABSTRACT

A multi-position body support, commonly known as a stander, supports a user in either a prone or supine orientation at any position from a substantially horizontal position to a substantially standing or vertical position. The multi-position body support comprises a tubular base having dual lock caster wheels for easy moving and positioning of the stander. A vertical support assembly, pivotally mounted to the tubular base, comprises a foot cylinder, knee support frame and a height adjustment frame. A foot support is mounted to the foot cylinder, a knee support is mounted to the knee support frame and a hip support, a trunk support and a head support can be mounted to the height adjustment frame. A padded strapping system secures the user within the pads and to the vertical support assembly. The foot supports can be rotated to aid in orienting the user in the prone or supine position. A pneumatic shock assembly connects the vertical support assembly to the tubular base frame and comprise a lockable pneumatic shock provides for urging the vertical support assembly from a horizontal position to a vertical position. A pedal is provided for unlocking the shock to adjust the angular orientation of the vertical support assembly in relation to the tubular base frame at any desired position between the horizontal and the vertical. A separate moveable tray is supported on dual lock caster wheels for use with the stander.

50 Claims, 9 Drawing Sheets

MULTI-POSITION BODY SUPPORT

BACKGROUND OF THE INVENTION

1. Field of the Invention

This invention relates to physical therapy aids for non-ambulatory patients. In one of its aspects, the invention relates to a multi-position stander for supporting a user in either a prone, supine, or vertical position.

2. Description of the Related Art

Persons with ambulatory problems, such as cerebral palsy victims, are often unable to stand. Often these persons are restricted to either sitting or lying positions. The inability to stand results in the person having both psychological and physical problems because the person is unable to interact with her peers and the inability to stand retards the bone development of the user and creates abnormal muscle tone.

The inability to interact at peer level and the retarded bone growth and the abnormal muscle tone can be corrected by placing the person in a standing position. Standing places the person at peer level and the person's weight is carried by her feet, which reduces the abnormal muscle tone, while allowing the person to be in hip and knee extension. The weight-bearing effects of standing stimulate bone growth and free the hands for activity and facilitates the user with head righting. Standing also provides a psychological benefit by providing a way for the user to interact and socialize with others at a peer level. Therefore, it is desirable to have a device, such as a stander, which can orient a user in the standing position.

Depending upon the particular needs of the user, it may be desirable to place the user in either a supine, prone or vertical position. The supine position Orients the user anywhere between a generally horizontal position and an almost vertical position. The generally horizontal position aids in transferring the user from a seated or lying position to the stander. In the prone position, much of the user's weight is carried from the user's upper body to the stander, reducing the weight borne by the user's legs. However, the prone position generally allows the user to comfortably work at a desk or other similar types of furniture. In the vertical position, the user bears much of her body weight by her legs which are supported by the stander.

Previous standers were dedicated to one of the three desired positions—supine, prone or vertical. An example of a prone stander is disclosed in U.S. Pat. No. 4,029,089, issued Jun. 14, 1977. The prone stander generally comprises a base having a tubular support post pivotally mounted to the base. Laterally adjustable chest support, hip support and knee supports are slidably mounted to the support post. A foot platform is slidably mounted to the support post. A telescoping brace connects the front portion of the frame to the support post to provide for changing the angular orientation of the support post with respect to the base over a limited range of movement and in discrete steps.

Previous standers are unsatisfactory because they require the physical therapist or the care giver to purchase a separate stander for the prone, supine and vertical position. No previous standers provided for a single stander that could position the user in the prone, supine or vertical position. Therefore, to obtain the benefits of the three positions, the physical therapist or the care giver would have to purchase a stander for each position. Requiring a single stander for each of the three positions increases the cost to the physical therapist or the care giver and reduces the convenience to the physical therapist and care giver for using the stander. Furthermore, many of the previous standers only provided for discrete adjustment of the support pads, which prevented the user from obtaining the most comfortable position of the supports.

SUMMARY OF THE INVENTION

The invention provides a simple and convenient-to-use stander that can position the user in the prone, supine and vertical position. The invention further provides a stander with an adjustable support pad system for the most comfortable positioning of the pads during use of the stander.

In accordance with the invention a multi-position body support comprises a base frame, vertical support assembly and body support pads. The base frame is supported by the floor. The vertical support assembly is pivotally mounted to the base frame and rotates about an axis of rotation which is generally horizontal with respect to the floor. The body support pads support the user of the multiposition body support on the vertical support assembly by a belt or strap system associated with the body support pads for securing the user within the body support pads. The adjustable brace extends between the base frame and the vertical support assembly and adjustably supports the vertical support assembly in a number of different positions between a substantially horizontal position and a vertical position with respect to the base frame.

Further, in accordance with the invention, the vertical support assembly comprises a pair of parallel support tubes and the body support pads are clamped to the parallel support tubes. A knee support frame having a pair of tubes is slidably received on the parallel support tubes. A height adjustment frame comprises a pair of tubes which are slidably received on the parallel support tubes. Preferably, the base frame has caster wheels which can independently lock the swivel movement of the wheel about a vertical axis and the rotation of the wheel about a horizontal axis.

Still further in accordance with the invention, the body support pads comprise foot pads, knee pads, hip pad, trunk pad and a head pad. The foot pads are mounted on the vertical support assembly and can rotate about a horizontal axis, rotate about a vertical axis, laterally adjust with respect to the vertical support assembly and are also adjustable toward and away from the axis of rotation of the vertical support with respect to the base. The knee pads are mounted to the vertical support assembly and can be adjusted vertically and laterally with respect to the vertical support assembly. The knee pads comprise a U-shaped foam member having a belt spanning the ends of the legs of the U-shaped foam member. The hip pad is mounted to the vertical support assembly and can be adjusted vertically with respect to the vertical support assembly. The hip pad comprises a U-shaped foam member having a belt spanning the ends of the legs of the U-shaped foam member. The trunk support pad is mounted to the vertical support assembly and can be adjusted vertically with respect to the vertical support assembly. The trunk support pad comprises a U-shaped foam member having a larger bite portion than the sides which are tapered for an ergonomic fit under the arms of the user.

A movable tray assembly is also provided according to the invention for use with the stander. The tray assembly has a frame with lockable casters for ease of selective movement of the frame on a floor surface and further has a tray pivotably mounted to the frame at a height for use by a user strapped into the stander in a prone position.

BRIEF DESCRIPTION OF THE DRAWINGS

The invention will now be described with reference to the drawings in which.

DETAILED DESCRIPTION OF THE PREFERRED EMBODIMENTS

Figure 1:
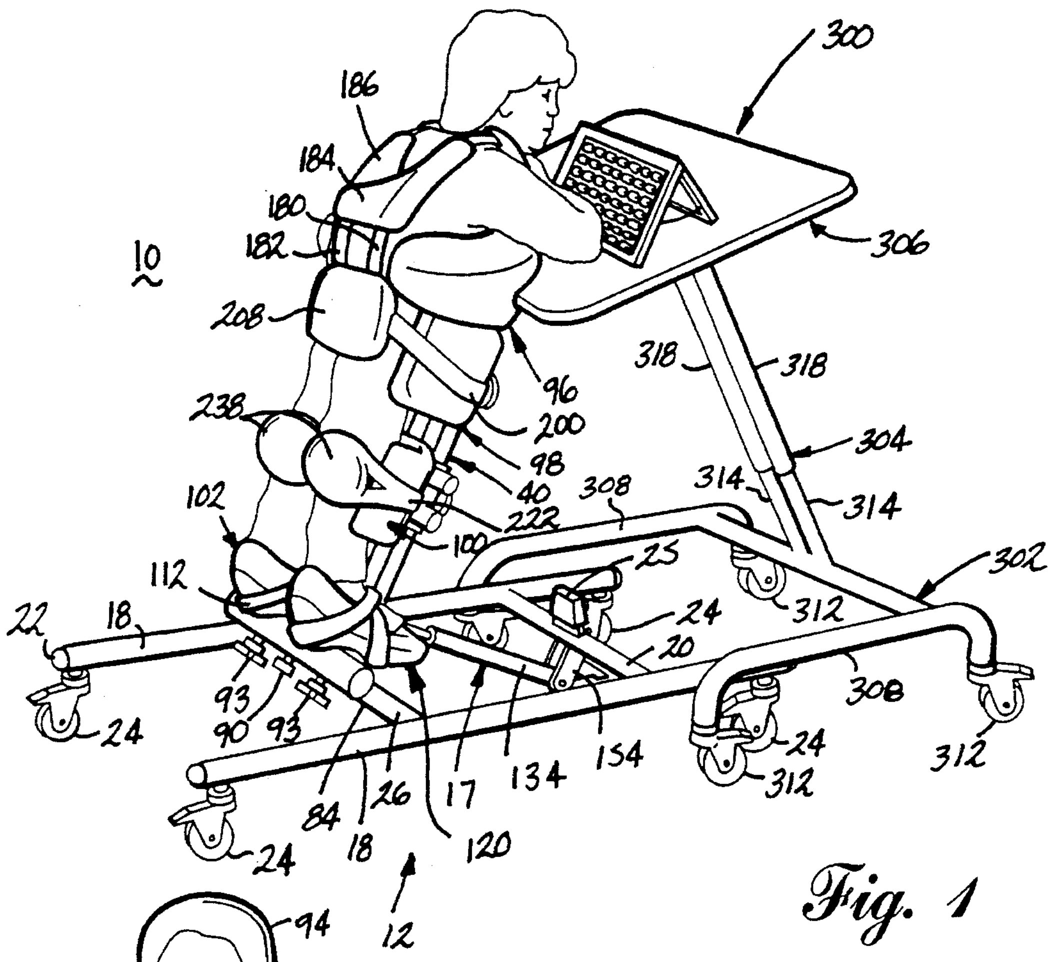
FIG. 1 is a perspective view of the multi-position body support according to the invention oriented in the prone position.
Figure 3:
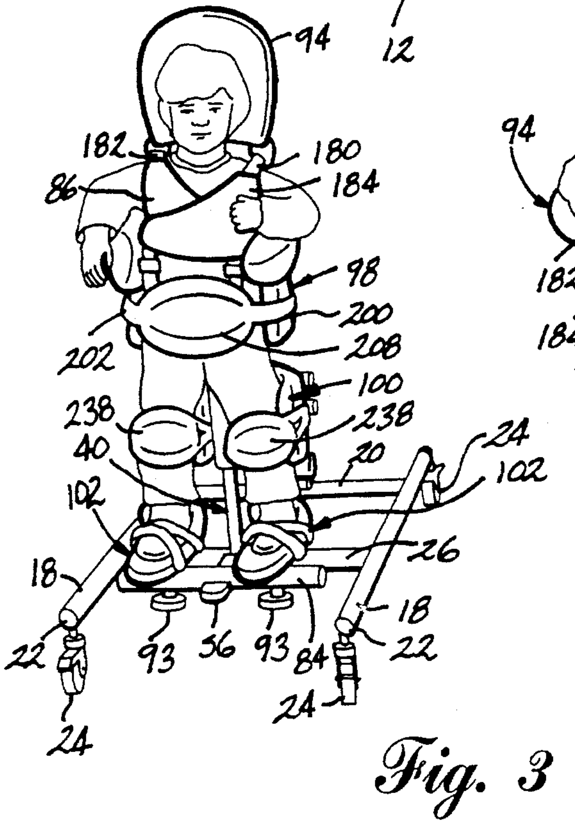
FIG. 3 is a perspective view of the multi-position body support according to the invention oriented in the vertical position.
Figure 2:
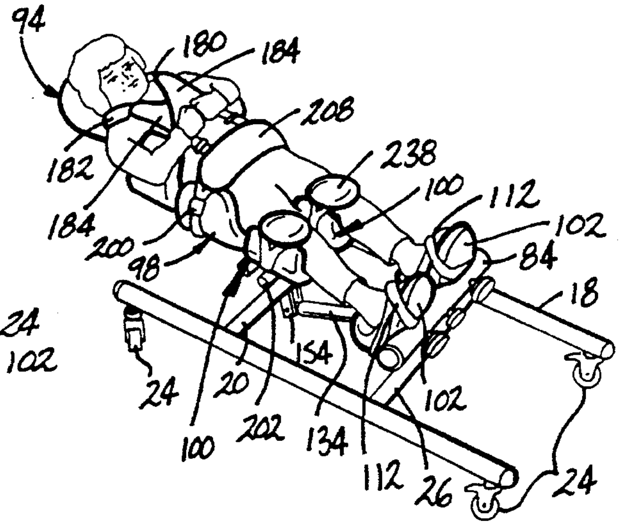
FIG. 2 is a perspective view of the multi-position body support according to the invention oriented in the supine position.

FIGS. 1–4 illustrate the multi-position body support 10, commonly known as a stander, in accordance with the invention. The multi-position body support 10 provides support for a user in an infinite number of positions between a substantially horizontal or lying position to a vertical or standing position, including the either prone (FIG. 1), supine (FIG. 2) or vertical position (FIG. 3). The multi-position body support can also secure the user lying on her back or lying on her stomach. The multi-position body support 10 comprises a base frame 12, vertical support assembly 14, body supports 16 and pneumatic shock assembly 17.

The base frame 12 comprises two longitudinal, horizontal, parallel tubular frame members 18, which are rigidly connected near one end by a transverse tubular cross member 20, preferably by welding. The tubular frame members 18 and tubular cross member 20 define a horizontal plane that is parallel to a floor. The ends of the tubular frame members 18 are closed by plugs 22. Dual lock caster wheels 24 are pivotally mounted to each end of the tubular frame members 18 and connect the frame to the floor. Preferably, the caster wheels are dual lock caster wheels that independently lock both the pivoting of the wheel and the rotation of the wheel. A rubber stop 25 is mounted to the tubular cross member 20 by a flange 23.

The base frame 12 further comprises aligned, tubular spacers 26. Each spacer is mounted to one of the tubular frame members 18 and extends inwardly into the interior of the base frame 12, defining a gap 27 between the tubular spacers 26. The end of each tubular spacer 26 is closed by a metal plug 28, which has an aperture 30. When the plug 28 is inserted into a tubular spacer 26, each bushing aperture 30 axially aligns with a tubular frame aperture 32 in the tubular frame members 18. An axle 34 with threaded axle ends 36, 38 is mounted through the aligned plug apertures 30 and tubular frame apertures 32. The threaded axle ends 36, 38 of the axle 34 receive lock nuts 37, which are covered by a nut cap 39.

The vertical support assembly 14 comprises a vertical support frame 40, knee support frame 42, height adjustment frame 44 and foot position cylinder 84. The vertical support frame 40 has a horizontal tubular base member 46 whose ends are plugged by bushings 48, which have bushing apertures 50. Two identical and parallel support tubes 52 are mounted to the tubular base member 46, preferably by welding, and defines the longitudinal axis of the vertical support assembly 14. One of the parallel support tubes 52 has a plurality of plunger receiving apertures 54 disposed longitudinally along the extent of the parallel support tubes 52 (FIG. 6), preferably on the portion of the tubes facing the tubular cross member 20. A tongue 56 is mounted to the tubular base member 46, normal to the parallel support tubes 52, preferably by welding, and defines an axis parallel to the longitudinal tubular frame members 18 and perpendicular to the longitudinal axis of the vertical support assembly 14. Aligned shock pin apertures 55 pass through the parallel support tubes 52. The shock pin apertures 55 are substantially parallel with and approximately four inches above the tubular base member 46.

The knee support frame 42 comprises connecting tubes 58, which have an inner diameter greater than the outer diameter of the parallel support tubes 52. A plunger support 60 is mounted near one end of the connecting tubes 58 (FIGS. 6 and 7) and are adapted to receive a support plunger 62, which is biased by a spring (not shown) into the plunger receiving apertures 54. Two parallel tubular cross members 64, oriented substantially normal to the parallel support tubes 52, are mounted to the connecting tubes 58 by parallel cross member mounting plates 66 and define a lateral or transverse axis for the vertical support assembly 14. The cross member mounting plates 66 are preferably welded to the connecting tubes 58 and are provided with aligned cross member apertures 68 through which the tubular cross members 64 are inserted. Preferably, the tubular cross members 64 are welded to the cross member mounting plates 66. The ends of the tubular cross members 64 are closed by plugs 70 which are similar to plugs 22.

The height adjustment frame 44 comprises a pair of parallel height adjustment tubes 72 with upper ends 76 and lower ends 80. The inner diameter of the height adjustment tubes is greater than the outer diameter of the parallel support tubes 52. The height adjustment tubes 72 are rigidly connected by a connecting plate 74, preferably at the upper end 76 of the height adjustment tubes 72. A plunger support 78 is mounted at the lower end 80 of one of the height adjustment tubes 72 (FIGS. 6 and 7) preferably the height adjustment tube 78 disposed above the parallel support tube 52 having the receiving apertures 54, for receiving and supporting a plunger 62. Plugs 82, similar to plugs 22, close the upper ends of the height adjustment tubes 72.

The vertical support frame 40 is connected to the base frame 12 by positioning the tubular base member 46 within the gap 27 between the tubular spacers 26 and aligning the bushing apertures 50 and 30 to the bushings 48 and plugs 28, respectively, with the tubular frame apertures 32. The axle 34 is inserted through the aligned tubular frame aperture 32 and bushing apertures 30 and 50. The axle 34 is positioned so that the threaded axle ends 36 and 38 extend slightly beyond the tubular frame members 18. Lock nuts 37 are threaded onto the threaded axle ends 36 and 38 to fasten the axle within the base frame 12. Nut caps 39 are placed over the lock nuts 37. The vertical support frame 40 can then pivot about the axle 34. The angular position of the vertical support frame can be adjusted to any desired position between a horizontal and vertical position.

The knee support frame 42 is slidably mounted onto the parallel support tubes 52 of the vertical support frame 40 by pulling out the spring biased plungers 62 and inserting the parallel support tubes 52 into the connecting tubes 58. The knee support frame 42 is slidably moved to the desired position and is fixed by releasing the plungers 62 which are then received in plunger receiving apertures 54 of the parallel support tubes 52. To reposition the knee support frame, the plunger 62 is pulled out to unlock the knee support frame 42, the knee support frame 42 is repositioned, and the plunger 62 is released.

In a similar manner, the height adjustment frame 44 is mounted to the parallel support tubes 52 of the vertical support frame 40. The parallel support tubes 52 are inserted into the lower ends 80 of the height adjustment tubes 72. To fix the position of the height adjustment frame 44, plungers 62 are inserted in the plunger receiving apertures 54 of the parallel support tubes 52 in the same manner as described above for the knee support frame 42.

The position of the knee support frame 42 and height adjustment frame 44 can be independently set by removing the plungers and adjusting either or both the knee support frame and height adjustment frame 44 to a desired position and reinserting the plungers 62. Thus, the multi-position body support 10 can be adjusted for users having a wide range of physical characteristics.

The foot position cylinder 84 is tubular and has opposed horizontally oriented slots 86 and lower slots 91 (FIG. 5) diametrically aligned with upper slots 92. The lower slots 91 and upper slots 92 extend longitudinally along a substantial portion of the foot positioning cylinder 84. An opening 88 (FIG. 6) is centrally located on the bottom of the foot position cylinder 84 between the opposed slots 86.

An off center cam roller 57 is mounted within the foot position cylinder 84. The off center cam roller 57 comprises a bracket 59, which pivotally mounts a roller 61 by an axle 63. The axle 63 is mounted above the center line of the roller 61 so the roller 61 acts as a camming device. An opening 65 is defined by the bracket 59 and the roller 61. The bracket 59 has a threaded opening 67 that aligns with an opening 88 (FIG. 5) disposed below the slot 86 and receives a mounting screw 90 for fixing the position of the foot position cylinder 84 with respect to the tongue 56.

The foot position cylinder 84 is mounted to the tongue 56 by a centrally disposed slot 86, which slidably receives the tongue 56. The off center cam roller 57 is mounted within the foot position cylinder 84 so that the opening 65 receives the tongue 56 as it passes through the slots 86. As the mounting screw 90 is tightened, the roller 61 cams against the tongue 56 to lock the foot position cylinder 84 with respect to the tongue 56.

The foot position cylinder 84 also has means for rotating the foot supports 102 (described in greater detail later) to provide for variable positioning of the user's feet with respect to the base frame 12. Preferably, the foot supports 102 can be rotated at least ±5 degrees with respect to the plane formed by the tongue 56. The foot pad pivoting means comprises a generally flat connection plate 69 and a wedge plate 71 having arcuate surfaces 73 and 83, respectively. The connection plate 69 and wedge plate 71 have apertures 75 and 77, respectively. The wedge plate 71 is disposed within the interior of the foot position cylinder 84 so that arcuate surface 83 abuts the inner surface of the foot position cylinder 84 and the aperture 77 is accessible through an upper slot 92. The arcuate surface 73 of the connection plate 69 is placed on the outer surface of the foot position cylinder 84 so that the apertures 75 and 77 are aligned. The mounting screws 90 are inserted through the lower slots 91 after placing a washer 79 and a spacer 81 onto the mounting screw 90. The screw is then passed through the aligned apertures 75 and 77 and screwed into the shoe as described below.

The angular orientation of the foot supports 102 are altered by moving the mounting screw 93, connection plate 69 and wedge plate 71 into the desired position and tightening the mounting screw 93 to secure the position of the foot supports 102. The spacer 81 prevents the threads of the mounting screw 93 from contacting edges of the lower slot 91 and transfers the pressure from the knob 93 to the clamp 71.

Figure 9:
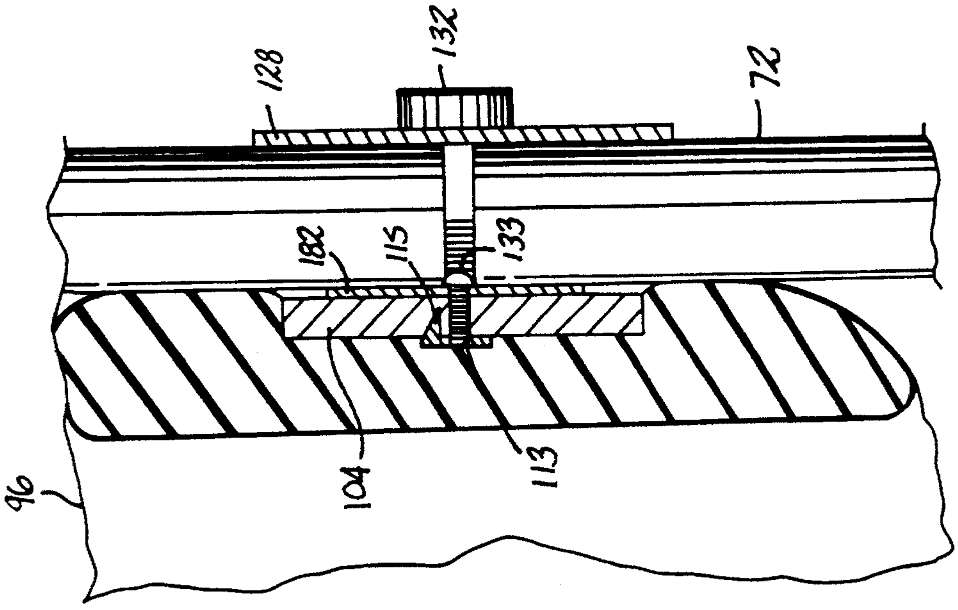
FIG. 9 is a sectional view along line 9—9 of FIG. 5.
Figure 12:
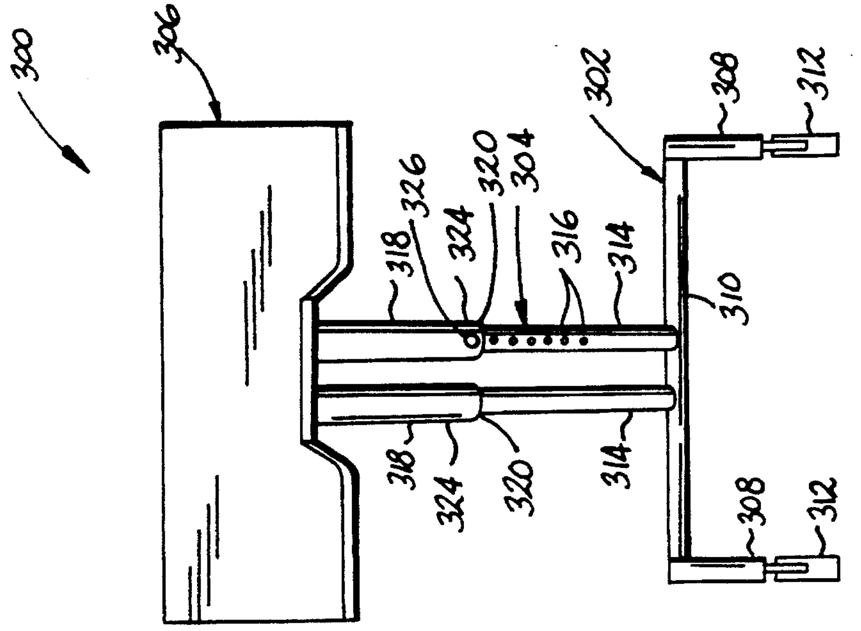
FIG. 12 is a rear view of the tray shown in FIG. 7.
Figure 10:
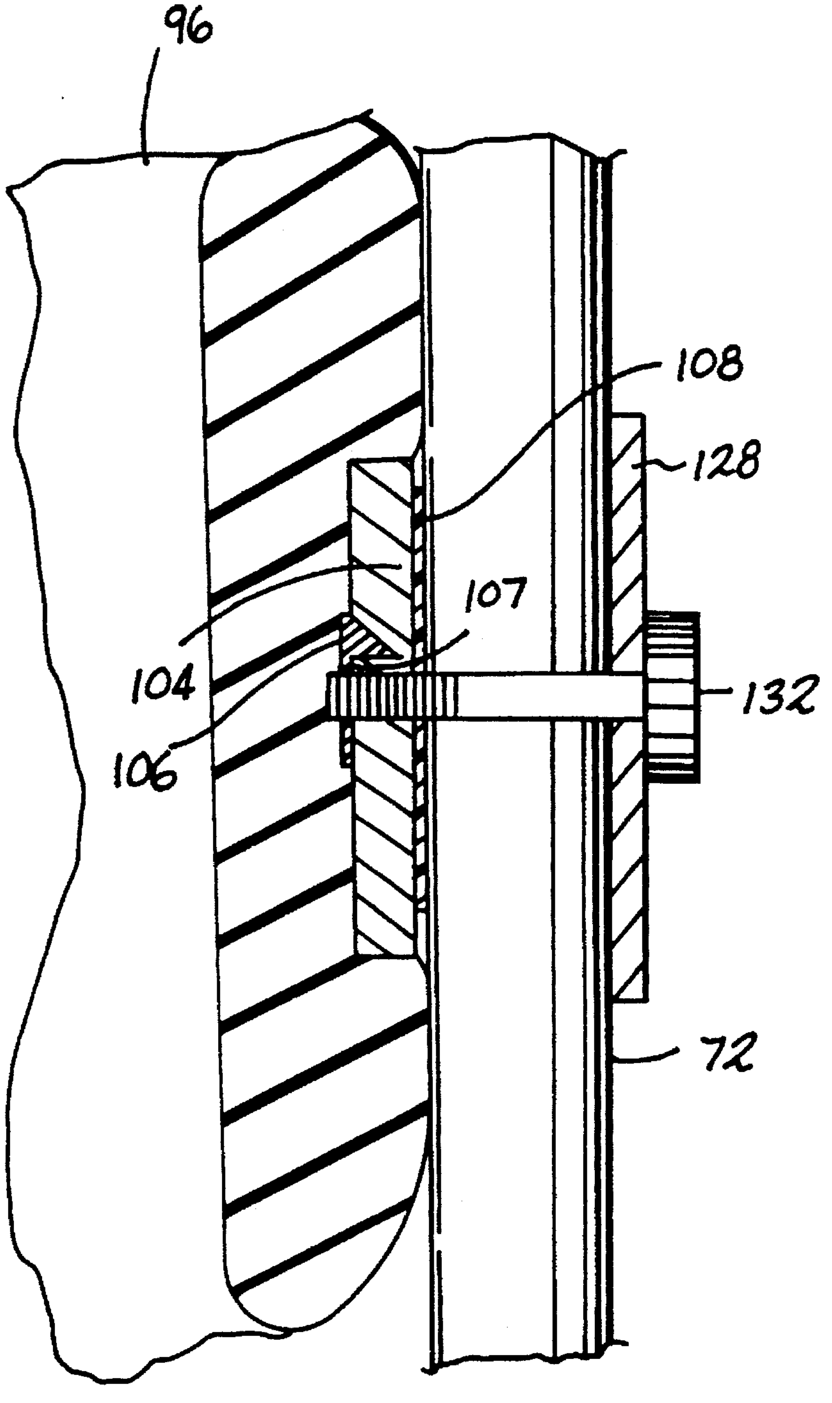
FIG. 10 is a sectional view along line 10—10 of FIG. 5.

Referring to FIGS. 4–7, the body supports 16 comprise head support 94, trunk support 96, hip support 98, knee supports 100, and foot supports 102. Each support is preferably molded from a structural urethane foam having a soft elastomer coating. Referring to FIG. 10, a mounting plate 104 is molded into the trunk support 96. The mounting plate 104 has a T-nut 106 with a T-nut opening 107 for receiving a mounting screw 132 and at least one other, but smaller, T-nut 115 with opening 113 for receiving a standard Phillips head screw 133 (FIG. 9). The T-nuts 106 in combination with screw 132 mount the trunk support to the vertical support 14. The T-nut 115 in combination with Phillips head screw 133 mount the padded strapping system (described in greater detail below) to the trunk support 96. The mounting plate 104 is preferably made from a wood or wood-by-product material. Each of the body supports have a similar mounting plate 104 with T-nuts as described above. The T-nut 115 is for mounting a padded strapping system to the body supports as disclosed in FIGS. 5–8 and discussed below.

Figure 4:
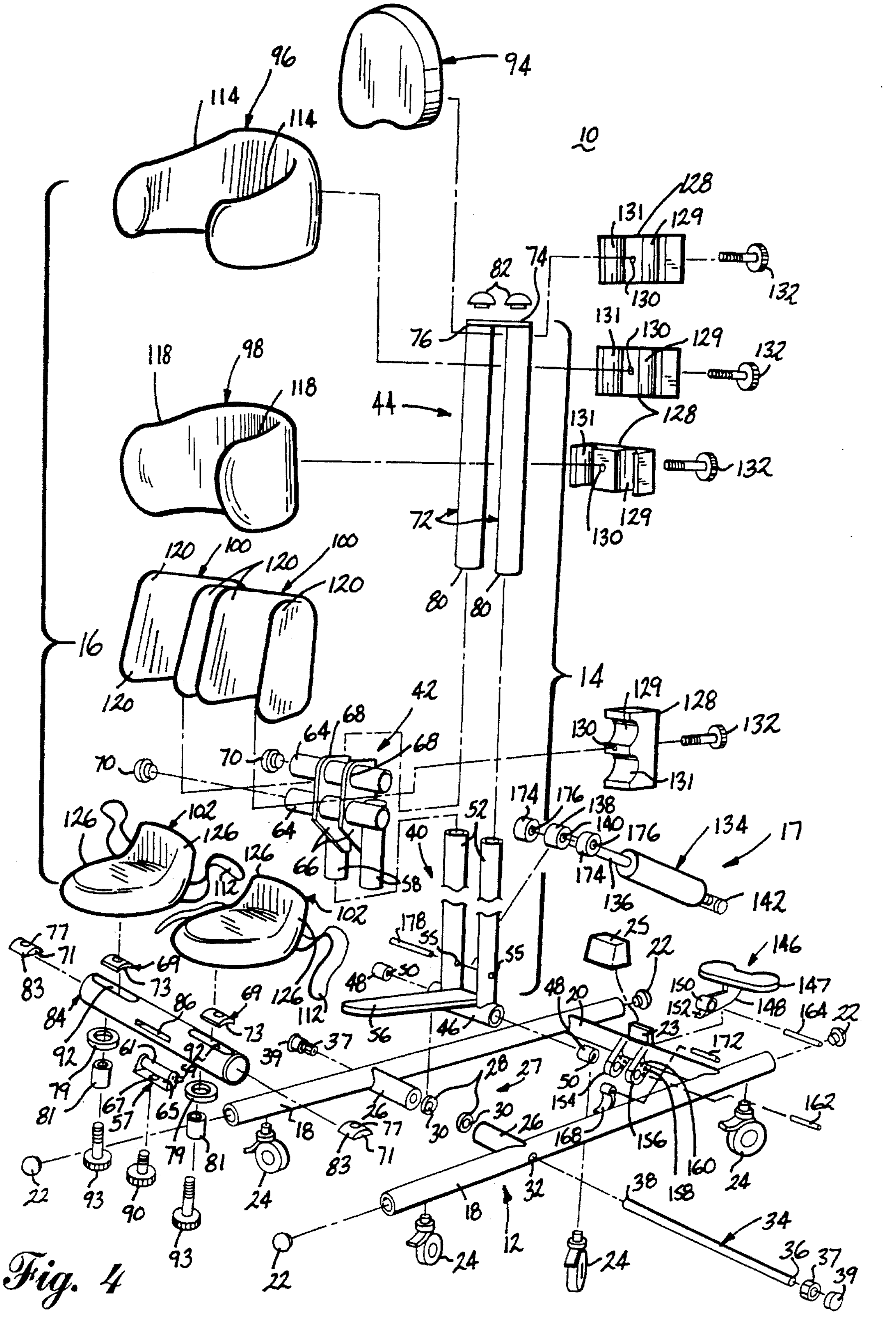
FIG. 4 is an exploded perspective view of the multi-position body support illustrated in FIGS. 1–3 with the padded strapping system not shown for clarity.

The trunk support 96, hip support 98, and knee supports 100 are combined with the padded strapping system, which has been removed from FIG. 4 for clarity. The foot supports 102 also have a mounting plate 104 with a T-nut 106 molded into the foot supports 102. The foot supports 102 have Velcro™ hook and loop fasteners 112 for securing the user's feet within the foot supports 102. Circular patches of Velcro™ hook and loop patches 117 are bonded to the heel portion of the foot supports 102. The Velcro™ hook and loop fasteners 112 are attached to the circular Velcro™ hook and loop patches and crossed over the upper surface of the foot supports 102 and wrapped around the bottom of the foot supports 102 where the ends of the Velcro™ hook and loop fasteners are hooked together to fasten the user's foot within the foot supports 102. The mounting plates 104 of the foot supports do not have T-nuts 115 for mounting the padded strapping system. Otherwise, the mounting plate for the foot support pads are identical to those disclosed above.

Figure 5:
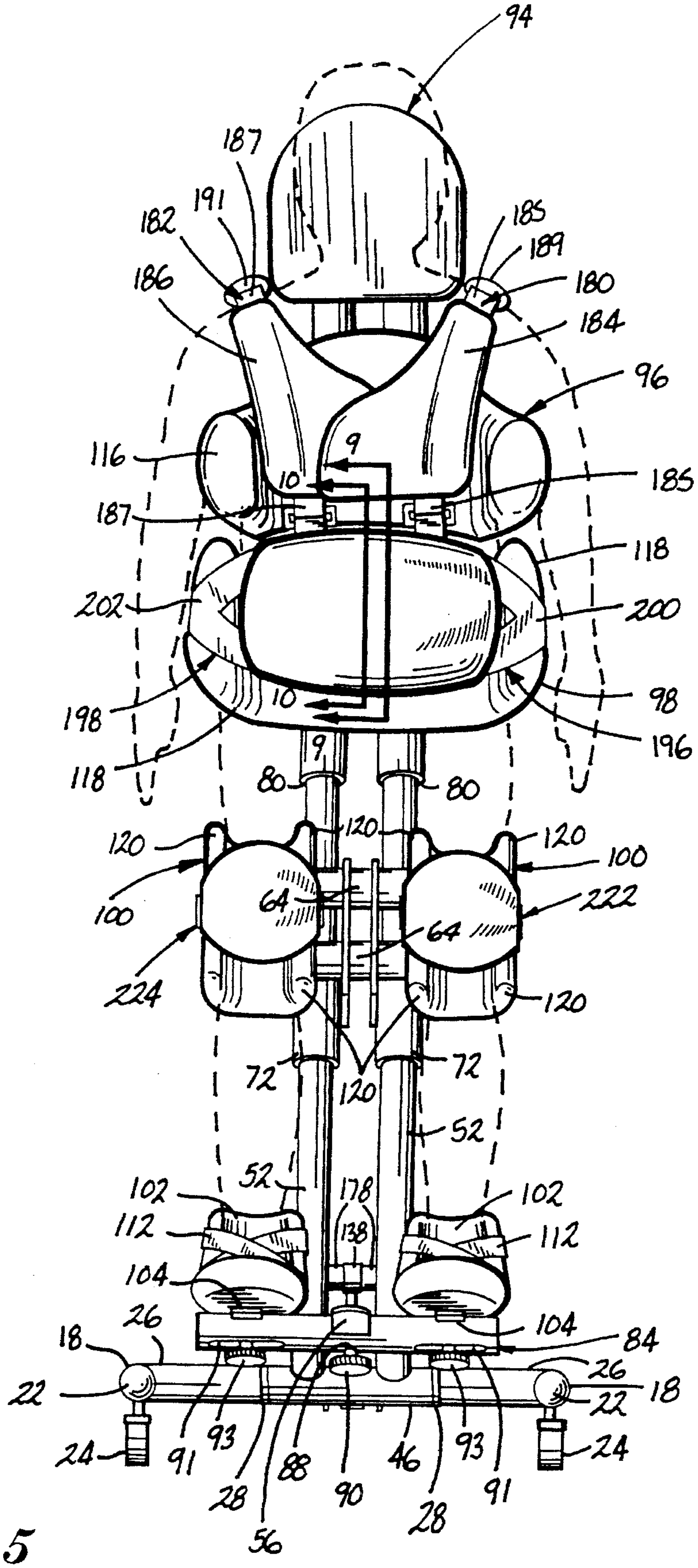
FIG. 5 is a front-view of the assembled multi-position body support shown in FIG. 1.
Figure 6:
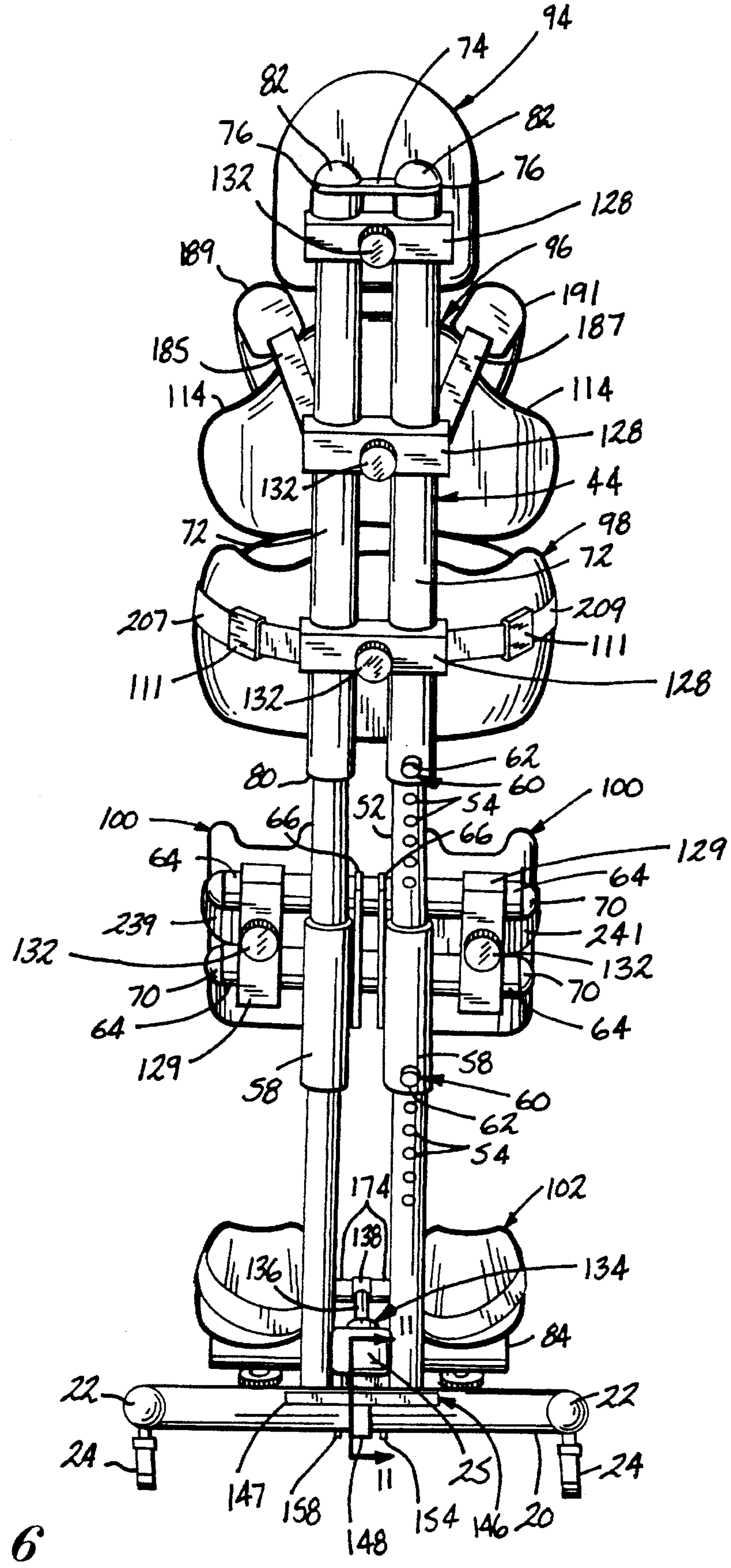
FIG. 6 is a rear view of the assembled multi-position body support shown in FIG. 1.
Figure 7:
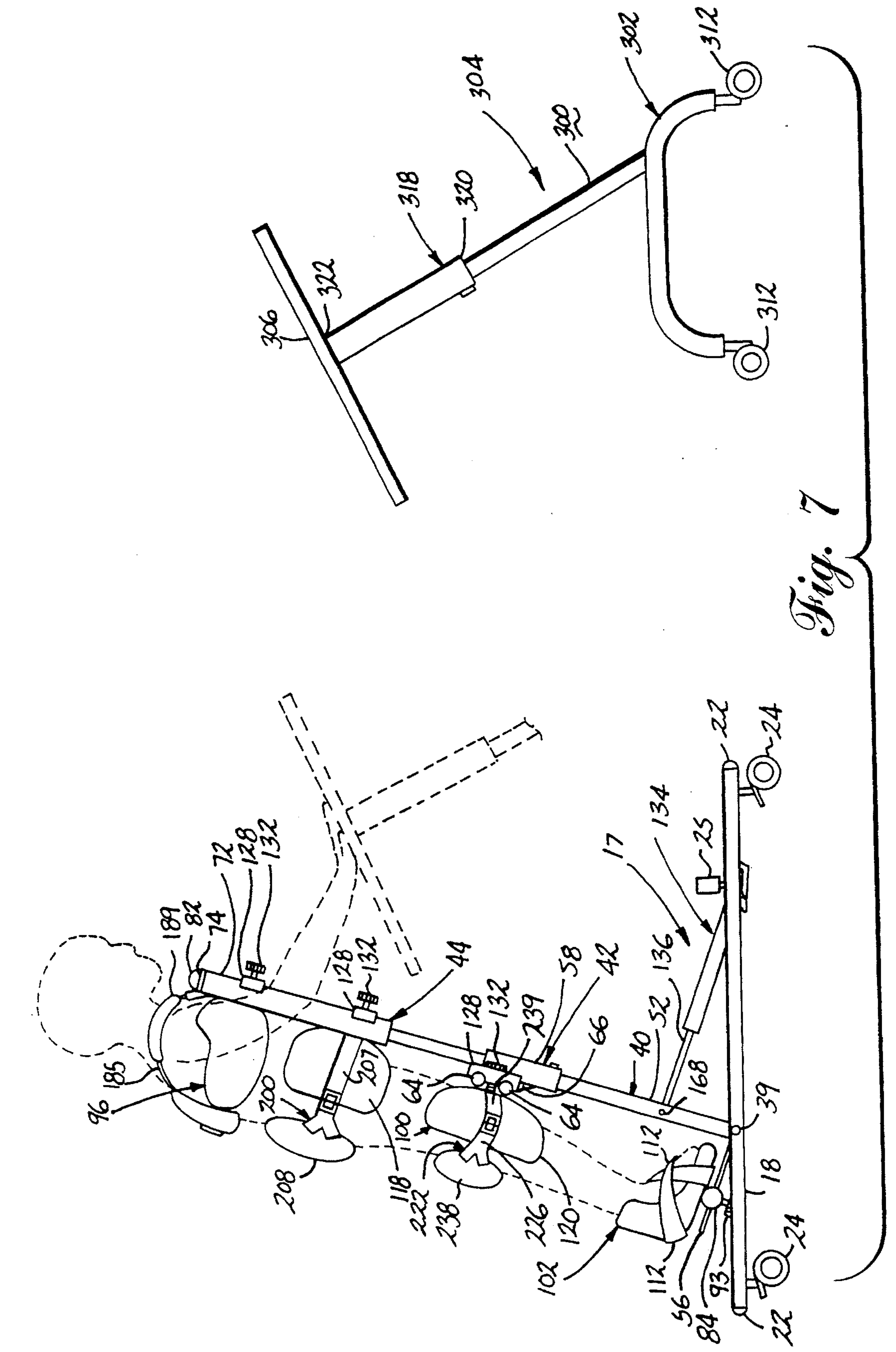
FIG. 7 is a side view of the assembled multi-position body support shown in FIG. 1 and an auxiliary tray assembly according to the invention.
Figure 8:
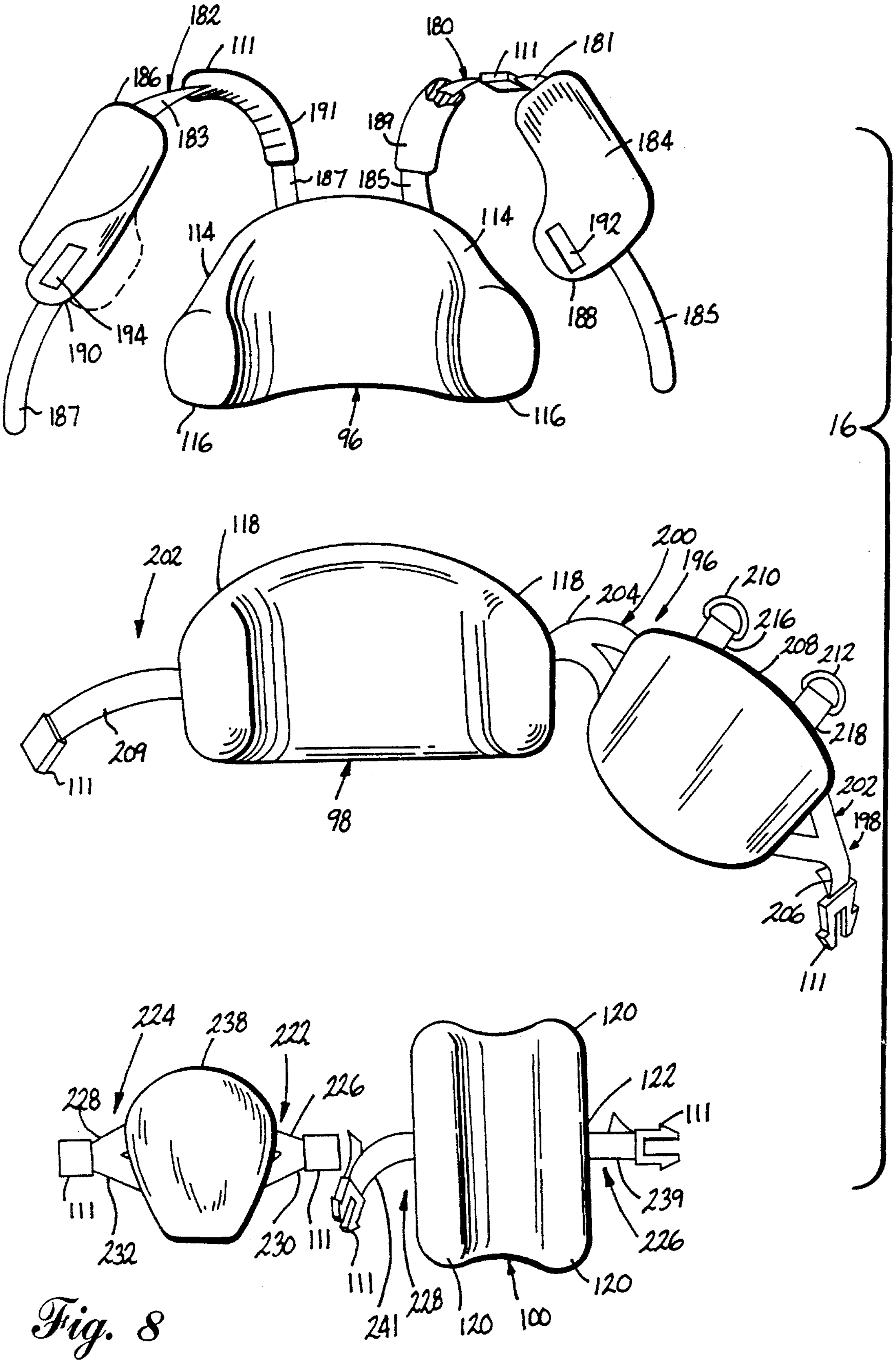
FIG. 8 is a partial sectional, assembly view of the support pads shown in FIG. 4 and showing an alternative belt design.

Referring to FIG. 8 specifically and FIGS. 4-7 generally, the body supports 16 can have a variety of shapes depending on their function and position. The head support 94 has a plate-like profile. The trunk support 96 is generally U-shaped and has reduced side portions 114 for a ergonomic fit under the user's arms while leaving the user's arms free (FIG. 7). The reduced side portions 114 taper to rounded ends 116. The hip support 98 is generally U-shaped and has side portions of constant width that taper to rounded ends 118. The knee supports 100 are generally U-shaped and have a pair of opposed side portions 120. The side portions 120 terminate at rounded ends 118. The foot supports 102 have a sole portion 124 from which extend upwardly and outwardly opposed side portions 126.

FIG. 9 illustrates the manner in which each of the head support 94, trunk support 96, hip support 98, and knee supports 100 are all connected to the vertical support assembly 14, although FIG. 6 only shows the connection between the trunk support 96 and the vertical support assembly 14. A second mounting plate 128, preferably made of polypropylene and having an aperture 130, is used in combination with a mounting screw 132 to clamp the support pads to the vertical support assembly 14. The second mounting plate 128 further has two arcuate depressions 129 and 131. The head support 94, trunk support 96 and hip support 98 are mounted to the height adjustment tube 72 of the height adjustment frame 44 by placing the body supports on one side of the height adjustment tubes 72 and the second mounting plate 128 on the opposite side of the height adjustment tubes 72 so that the height adjustment tubes 72 are positioned within the arcuate depressions 129, 131 and the aperture 130 of the second mounting plate 128 is aligned with T-nut 106. The mounting screw 132 is inserted through the aperture 130 of the second mounting plate 128 and is threaded into the T-nut 106 of the mounting plate 104 of the body supports and tightened. The position of the body supports can be varied by loosening the mounting screw 132 and sliding the body supports and the second mounting plate 128 to the desired position along the height adjustment tubes 72 of the height adjustment frame 44 and re-tightening the mounting screw 132 to fix the position of the body supports.

The knee supports 100 are mounted to the knee support frame 42 by placing the knee supports 100 on one side of the tubular cross member 64 to the outside of the cross member mounting plates 66 and placing the second mounting plate 128 on the opposite side of the tubular cross members 64 so the tubular cross members 64 are positioned within the arcuate depressions 129, 131. The mounting screw 132 is then inserted through the aperture 130 of the second mounting plate 129 and threaded into the T-nut 106 of the mounting plate 104 on the knee supports 100. The lateral position of the knee supports 100 can be adjusted by loosening the mounting screw 132 and sliding the knee supports 100 and second mounting plate 128 laterally with respect to the cross member mounting plates 66 and re-tightening the mounting screw 132 when the knee supports 100 are in the desired position.

The foot supports 102 are mounted to the foot position cylinder 84 by passing the mounting screws 93 through upper slots 92 in the foot position cylinder 84 and threading the mounting screws 93 into the T-nut 106 of the mounting plate 104 and the sole portion 124 of the foot supports 102. The lateral position of the foot supports 102 can be adjusted by loosening the mounting screws 93 and moving the foot supports 102 along the upper slot 92 until the desired position is reached and then tightening the mounting screws 93. The longitudinal position of the foot supports 102 with respect to the tongue 56 can also be adjusted by loosening the mounting screw 90 and sliding the foot position cylinder 84 along the tongue 56 until the desired position is reached and then tightening the mounting screw 90. Thus, the foot supports 102 are mounted to the vertical support assembly 14 for adjustment toward and away from the axis of rotation between the vertical support assembly 14 at the base frame 12, for adjustment about an axis perpendicular to the axis of rotation between the vertical support assembly 14 and the base frame 12, and for adjustment toward and away from each other and for the rotation about a horizontal axis.

Referring to FIGS. 8 and 9, the trunk support 96 has trunk straps 180 and 182 which are mounted to the mounting plate 104. FIG. 9 illustrates the mounting of trunk strap 182. The mounting of all the other straps for the body supports is similar to the mounting of trunk strap 182. In FIG. 9, the trunk strap 182 is mounted to the mounting plate 104 by a phillips head screw 133 that threads into a T-nut 115 after passing through a T-nut opening 113 in the end of the trunk strap 182.

Referring to FIG. 8, the trunk straps 180 and 182 are divided into two sections: a back section 181, 183 and a front section 185, 187, respectively. Snap-fit buckles 111 adjustably connect the front sections 185, 187 to the back sections 181, 183, respectively. The snap-fit buckles are enveloped by shoulder pads 189, 191, respectively, which are sewn to the trunk straps 180, 182, respectively. The ends of the front sections 185 and 187 have Velcro™ hook and eye fasteners attached thereto. Referring to FIG. 8, trunk restraint pads 184 and 186 are connected to the trunk straps 180 and 182, respectively. Trunk restraint pads 184 and 186 are mirror images of each other and have a flap portion 188 and 190, respectively, to which is bonded Velcro™ hook and loop fasteners 192 and 194, respectively.

The hip support 98 is combined with a hip restraint pad 208, which has Y-shaped hip straps 196 and 198. The Y-shaped hip straps 196 and 198 have a split or V-portion 200 and 202, respectively, which converge to a stem portion 204 and 206, respectively. The stem portions 204, 206 of the Y-shaped hip straps 196, 198 are connected by snap-fit buckles 111 to the web straps 207, 209 of the hip support 98. The web straps 207, 209 are connected to the hip support 98 by T-nuts and screws in the same manner as described above for the trunk support 96. Two sets of D-rings 210 and 212 are connected to the hip restraint pads 208 by webs 216 and 218, respectively, which are bonded to the hip restraint pad 208. The ends of trunk strap front sections 185 and 187 are adapted to be received within the D-rings 210 and 212, respectively, and secured by the Velcro™ hook and eye fasteners.

The knee supports 100 are combined with knee restraint pads 238, which have a pair of Y-shaped straps 222 and 224. The Y-shaped straps 222, 224 have split portions 226 and 228, respectively, that converge to stem portions 230 and 232, respectively. The stem portions 230, 232 are connected to web straps 239, 241 of the knee supports 100. The web straps 239, 241 are connected to the mounting plate 104 by T-nuts and Phillips head screws in the same manner as described above for the trunk support 96. The split portions 226, 228 are connected to the knee restraint pads 238 by snap-fit buckles 111 connect the stem portions 230, 232 to the web straps 239, 241 to connect the knee restraint pads 100 to the knee supports 100.

In use, when a user is positioned within the body supports 16 substantially as shown by the phantom lines in FIG. 5, the trunk straps 180 and 182 of the trunk support 96 are placed over the user's shoulder and the shoulder pads 189, 191 are adjusted on the trunk straps 180 and 182 so the snap-fit buckles 111 do not directly contact the user's shoulder. The trunk restraint pads 184 and 186 are positioned in abutting relationship with respect to the user's body and connected to each other by the Velcro™ hook and loop fasteners 192 and 194. By fastening the Velcro™ hook and loop fasteners 192 and 194, the flap portion 190 overlies the flap portion 188 and the trunk straps 180 and 182 are connected horizontally through the Velcro™ hook and loop fastened trunk restraint pads 184 and 186.

The hip restraint pad 208 is then positioned against the user's body opposite the hip support 98 and fastened by connecting the snap-fit buckle 111 to securely fasten the user between the hip support 98 and the hip restraint pad 208. The ends of the trunk straps 180 and 182 are then inserted into the D-rings 210 and 212 and adjusted before fastening by the Velcro™ hook and loop fasteners. The combination of the trunk straps 180 and 182 connected to the hip restraint pad 208 and to each other by the trunk restraint pads 184 and 186 effectively creates a harness to restrain the user within the trunk support 96 and the hip support 98.

To secure the user's knees, the knee restraint pad 238 is placed against the user's knee on the opposite side of the knee support 100 and connected to the knee support 100 by fastening the snap-fit buckles 111 and adjusting the stem portions 230, 232 with respect to the snap-fit buckles 111 to draw the knee restraint pad 238 snugly against the user's knee.

The strapping system as described above securely restrains the user within the trunk support 96, hip support 98 and the knee supports 100 without direct contact between the straps and the user's body. The trunk restraint pads 184, 186, hip restraint pad 208 and knee restraint pads 238, instead of the straps, contact the user's body.

Figure 11:
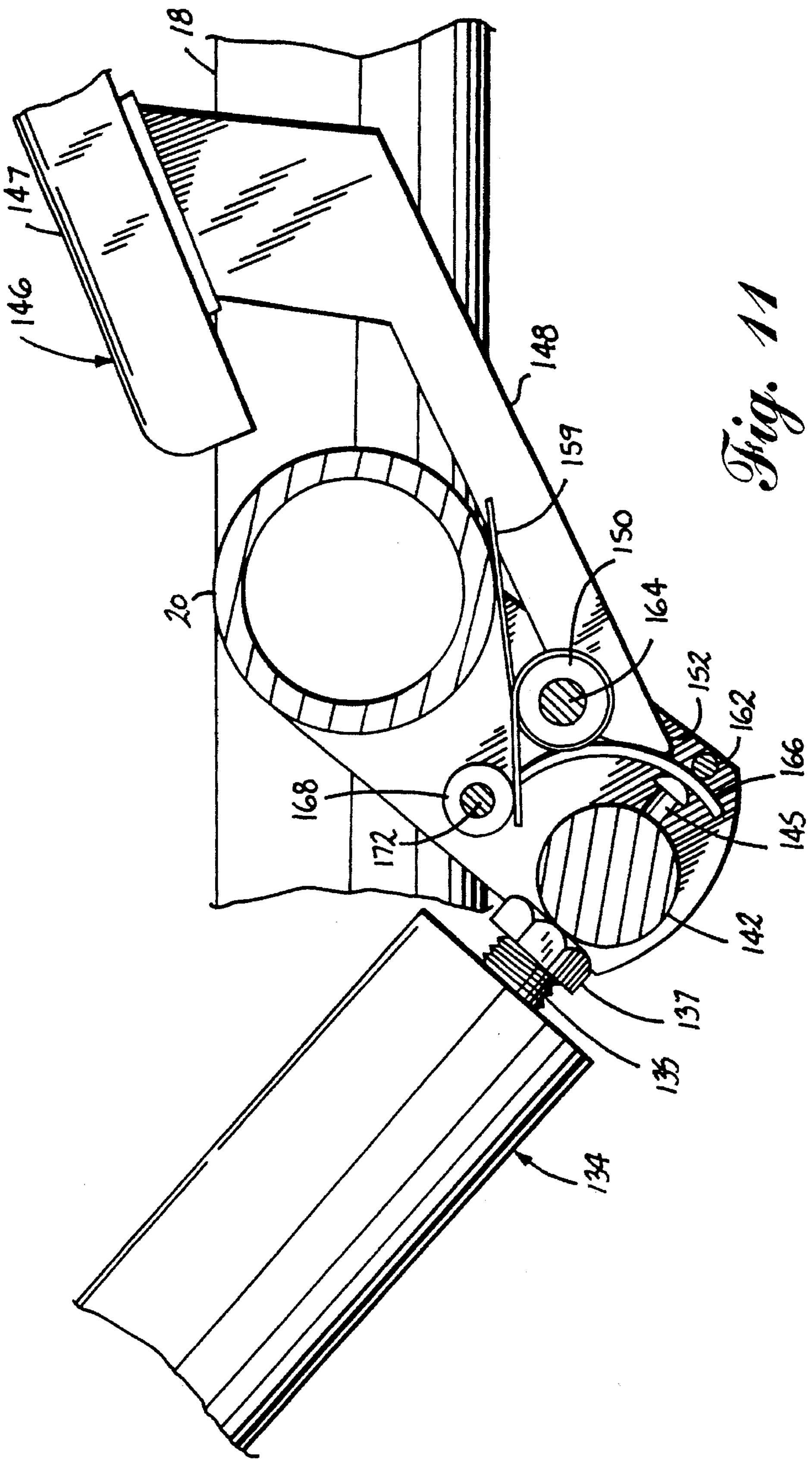
FIG. 11 is a sectional view along line 11—11 of FIG. 6.

Referring to FIGS. 4 and 11, the pneumatic shock assembly 17 comprises a pneumatic cylinder or shock 134, which is preferably a nitrogen filled gas shock. The pneumatic shock 134 is well known and can be purchased from Suspa Compart AG in Altdorf, Germany. The pneumatic shock 134 is connected between the base frame 12 and the vertical support assembly 14 and controls and locks the angular orientation of the vertical support assembly 14 with respect to the base frame 12.

The pneumatic cylinder or shock 134 has a spring shaft 136 which extends outwardly from the cylinder and terminates at a shock ring 138 having an aperture 140. The other end of the pneumatic cylinder or shock 134 has a tubular threaded extension 135. A mushroom-shaped activating pin 145 is connected to the pneumatic cylinder or shock 134 and extends through the tubular threaded extension 135. A threaded pin connector 142 has a diametrically oriented threaded aperture 143 into which the tubular threaded extension is threaded. The mushroom-shaped activating pin 145 extends through the threaded pin connector 142 via the threaded aperture 143. A lock nut 137 secures the threaded pin connector 142 to the tubular threaded extension. Pressing on the mushroom-shaped activating pin 145 unlocks the pneumatic cylinder or shock 134 so the pressurized gas urges the spring shaft 136 outwardly. The spring shaft 136 is thus biased outwardly of the cylinder by gas within the cylinder and is locked into an adjusted position when the mushroom-shaped activating pin 145 is in the extended position. The spring shaft 136 can be retracted by depressing the mushroom-shaped activating pin 145 and rotating the vertical support assembly to the position shown in FIG. 2 against the pressure of the gas in the cylinder. A mechanical locking, telescoping tube assembly can be used in lieu of a gas cylinder.

A foot pedal 146 for actuating the mushroom-shaped activating pin 145 to lock and unlock the pneumatic cylinder or shock 134 has a foot plate 147 from which extends a beam 148 with an aperture 150 and terminating in an actuator 152. A shock pin activator 166 separates the actuator 152 of the foot pedal 146 and the mushroom-shaped activating pin 145 of the pneumatic cylinder or shock 134. The shock pin activator 166 has a curved radius portion 170 and an aperture 168.

The pneumatic shock assembly 17 is connected at one end to the tubular cross member 20 of the base frame 12 by the flanges 154, which are preferably welded to the tubular cross member 20. The flanges 154 have pin connector aperture 156, pedal aperture 158 and shock pin aperture 160. The threaded pin connector 142 is positioned between the flanges 154 and aligned with the pin connector apertures 156. Opposed snap rings (not shown) connect the threaded pin connector 142 to the flange 154. The foot pedal 146 is connected to the flanges 154 by a bolt 164 passing through the pedal apertures 158 and the aperture 150 of the foot pedal 146. The actuator 152 of the foot pedal 146 is connected to the mushroom-shaped activating pin of the pneumatic cylinder or shock 134 by the curved or radius portion 170 of the shock pin activator. The shock pin activator 166 is mounted to the flanges 154 by passing a threaded bolt 172 through the threaded shock pin aperture 160 and the aperture 168 of the shock pin activator 166. A mounting pin 162 is mounted to the flanges 154 to support one end of the curved or radius portion 170 of the shock pin activator 166.

The pneumatic shock assembly 17 is connected to the vertical support frame 40 by the spring shaft 136 of the pneumatic cylinder or shock 134, which is pivotally connected to the height adjustment tubes 72 of the vertical support frame 40. Shock pin bushings 174 having apertures 176 are positioned on opposite sides of the shock ring 138. The shock pin bushings 174 and the shock ring 138 are positioned between the parallel support tubes 52 so that the apertures 140, 176 align with the shock pin apertures 55 of the parallel support tubes 52. A shock pin 178 is inserted through the aligned apertures to pivotally mount the spring shaft 136 to the vertical support frame 40.

The foot pedal 146 can be biased by a torsion spring 159 (FIG. 11) or other similar device so that the foot plate 147 is urged upwardly and almost normal to the horizontal plane of the base frame 12. Thus, an operator must actively seek to engage the pedal so as to lessen the possibility of inadvertently unlocking the pneumatic cylinder or shock 134 by unintentionally contacting the foot pedal 146. The curved or radius portion of the shock pin activator 166 is preferably curved along the arc which the mushroom-shaped activating pin 145 of the pneumatic cylinder or shock 134 traverses as the pneumatic cylinder or shock 134 is rotated about the mounting pin 162 during the raising and lowering of the vertical support assembly 14 with respect to the base frame 12. The actuator 152 of the foot pedal bears against the curved or radius portion 170 of the shock pin activator 166 when the foot pedal 146 is depressed and rotated about the bolt 164. Thus, regardless of the angular orientation of the mushroom-shaped activating pin 145 with respect to the actuator 152 of the foot pedal 146, the actuator 152 can actuate the mushroom-shaped activating pin 145 and unlock the pneumatic cylinder or shock 134 by acting against the curved or radius portion 170 of the shock pin activator 166, which, in turn, depresses the mushroom-shaped activating pin 145 to unlock the pneumatic cylinder or shock 134.

In operation, it is initially desirable to lower the vertical support assembly 14 to a substantially horizontal position providing for more easily transferring the user from a chair or bed and into the multi-position body support 10. To lower the vertical support assembly 14, the operator will grasp the vertical support assembly 14 and depress the foot pedal 146, which unlocks the pneumatic cylinder or shock 134 as described above. With the pedal depressed, the operator will urge the vertical support assembly 14 downwardly against the force of the pneumatic cylinder or shock 134 until the vertical support assembly 14 contacts the rubber stop 25 on the tubular cross member 20. The pedal is released to lock the pneumatic shock 134 and the vertical support assembly in the horizontal position.

The user is then transferred from the chair or bed into the body supports 16 of the multi-position body support 10. If the user is to be placed in the prone orientation, the foot supports 102 are rotated on the foot position cylinder 84 so that they face the pneumatic shock assembly 17 and the head support 94 is removed or not mounted to the vertical support assembly 14. However, if the user is to be placed in the supine orientation, the foot supports 102 are pivoted on the foot position cylinder 84 so they face away from the pneumatic shock assembly 17 and the head support 94 is mounted to the height adjustment frame 44 as described above to support the back of the user's head. The trunk support 96, hip support 98 and knee supports 100 are mounted to the vertical support assembly 14 regardless of the prone or supine orientation of the user.

For both the prone and supine orientations, the relative positions of the body supports 16 are initially positioned in the manner described above by measuring the user and adjusting the supports to match the body dimensions of the user. After the user is transferred to the multi-position body support 10 and placed within the body supports 16, final adjustments to the positions of the body supports 16 are independently made in the manner previously described. The initial or approximate positioning is first accomplished by moving the knee support frame 42 and height adjustment frame 44 with respect to the parallel support tube 52. The final or fine adjustments are made by moving the body supports 16. Thus, the multi-position body support can be very accurately adjusted to each individual, providing the user with the greatest amount of comfort.

The user is then secured to the body supports by fastening the padded strapping system of the trunk support 96, hip support 98, and knee supports 100 and the Velcro™ hook and loop fasteners 112 for the foot supports 102 in either of the methods previously described.

Once the user is secured within the body supports 16, the operator can position the user at any angular orientation with respect to the plane of the base frame 12 from a substantially horizontal or lying position to a substantially vertical or standing position. Preferably the angular orientation can vary between 15° to 90° with respect to the base frame 12. Advantageously, the body supports 16, especially the trunk support 96 are positioned to support the user at any position in the possible range so that the user has uninhibited use of her arms as shown by the dashed lines in FIGS. 5 and 7.

To move the user to the desired angular position, the operator grasps the vertical support assembly 14 and depresses the foot pedal 146 to unlock the pneumatic cylinder or shock 134. While the pedal is depressed, the operator urges the vertical support assembly 14 to the desired position with the aid of the pneumatic cylinder or shock 134. The angular positioning of the user is infinite within the range of movement from the lying position to the standing position because the vertical support assembly 14 can be moved to any point between the lying position and the horizontal position, not just at discrete points. Thus, the multi-position body support 10 increases the comfort of the user and utility to the operator by the accurate positioning. Further, the adjustment is made very easily by simply depressing the foot pedal and guiding the vertical support assembly to its adjusted position.

Depending on the needs of the user, the angular and lateral position of the user's feet mounted within the foot supports 102 can be altered in the manner previously described. Furthermore, the lateral position of the user's knees can also be altered in the manner previously described.

After the user is located at the desired position, the user can be moved to the desired area by rolling the multi-position body support 10 on the dual lock caster wheels 24. Once the multi-position body support 10 is in the desired location, the pivoting and rotation of the dual lock caster wheels 24 can be locked. The multi-position body support 10 holding a user is often located near a work surface so that the user can work or engage in every day tasks.

For example, the multi-position body support 10 can be used in combination with a variety of other furniture pieces, such as the wheeled tray 300 shown in FIGS. 6 and 10. The wheeled tray 300 comprises a tubular base 302, vertical positioning assembly 304, and table top 306. The tubular base 302 further comprises parallel tubular members rigidly connected by a tubular cross member 310, which is preferably welded to the tubular members 308. Caster wheels 312 are mounted at each end of the tubular members 308 and preferably are dual locking caster wheels similar to dual lock caster wheels 24. The vertical positioning assembly 304 comprises parallel support tubes 314, which are welded to the tubular cross member 310 and have a plurality of plunger receiving apertures 316.

A pair of parallel positioning tubes 318 having an inner diameter greater than the outer diameter of the parallel support tubes 314 and upper end 322 and lower end 320 are slidably mounted over the parallel support tubes 314 at their lower ends 320. The upper end 322 of the parallel positioning tubes 318 are pivotally mounted to the table top 306 by an adjustment means (not shown), which adjusts the angle of the table top 306 with respect to the parallel positioning tubes 318. The parallel positioning tubes 318 have a spring biased plunger support 324 for receiving and supporting a plunger 326. The plunger support 324 has a plunger aperture 328, which receives plungers 326.

The vertical position of the table top 306 can be adjusted by sliding the parallel positioning tubes 318 along the parallel support tubes 314 until the desired height is reached. The plungers 326 are then inserted into the plunger supports 324 and through the plunger aperture 328 into the plunger receiving apertures 316 in the parallel support tubes 314 to fix the vertical position of the table top 306. The angle of the table top 306 with respect to the parallel positioning tubes 318 is then adjusted by the adjustment means.

The wheeled tray 300 can be used in combination with the multi-purpose body support as shown by the phantom lines in FIG. 7. Preferably, the distance between the tubular members 308 of the tubular base 302 is greater than the distance between the outer sides of the tubular frame members 18 so that the wheeled table can be rolled into the desired position close to the user secured in the multi-position body support 10. When the wheeled tray 300 is in the desired position, the caster wheels 312 can be locked to retain the wheeled tray in the desired position. The position of the table top can be adjusted before or after the wheeled tray is rolled into the desired position in the manner described above.

The invention provides a sturdy body support or stander which can be easily and quickly adjusted to fit different sized users. The stander can support the user in a supine, prone, or vertical position in any orientation between horizontal and vertical position. The angular orientation is easily adjustable by simply grasping the vertical support assembly, depressing the foot pedal 146 and adjusting the vertical support assembly to a proper height. The invention further provides a frame which is ambulatory for ease of movement of the user, yet which is securely lockable in a given location. Finally, the invention provides a combination stander and tray which are moveable with respect to each other for a variety of functions.

Reasonable variation and modification are possible within the spirit of the foregoing specification and drawings without departing from the scope of the invention.

The embodiments for which an exclusive property or privilege is claimed are defined as follows:

1. In a multi-position body support comprising:

a base frame adapted to be supported by a floor;

an elongated vertical support frame which is pivotally mounted at one end thereof to the base frame for rotation about a horizontal axis at the one end thereof;

body supports mounted to the vertical support frame for supporting a user on the vertical support frame, the body supports having fasteners for securing the user to the body supports, the body supports including a pair of foot supports, each of which is mounted on the vertical support frame at said one end and each of which is adapted to retain a foot of a user supported by the body support;

an adjustable brace between the base frame and the vertical support frame and having a first and a second portion which are adjustable with respect to each other to lengthen or shorten the length of the brace to control the angular orientation of the vertical support frame with respect to the base frame; and the improvement which comprises:

the body supports comprise a head support which is removably mounted to the vertical support frame to support the head of a user in a supine position; and the brace is positioned on the base frame and on the vertical support frame so that the brace adjustably supports the vertical support frame between a substantially horizontal position and a vertical position with respect to the base frame.

2. The multi-position body support of claim 1 wherein the vertical support frame comprises a pair of parallel support tubes to which are clamped the body supports.

3. The multi-position body support of claim 2 wherein the vertical support frame further comprises a knee support frame having a pair of tubes which are slidably received on the parallel support tubes and releasable fasteners for adjustable positioning of the knee support frame on the adjustable parallel support tubes.

4. The multi-position body support of claim 2 wherein the vertical support frame further comprises a height adjustment frame having a pair of tubes which are slidably received on the parallel support tubes and releasable fasteners for adjustable positioning of the height adjustment frame on the parallel support tubes.

5. The multi-position body support of claim 2 wherein the base frame has caster wheels with locks for locking the rotational movement of each caster wheel about a vertical axis and locking the rotation of each caster wheel about a horizontal axis.

6. The multi-position body support of claim 2 wherein the body supports further comprise a pair of foot supports, each of which is mounted on the vertical support frame for rotation about a horizontal axis.

7. The multi-position body support of claim 6 wherein the foot supports are each mounted to the vertical support frame for rotation about a vertical axis.

8. The multi-position body support of claim 7 wherein the foot supports are each mounted to the vertical support frame for lateral adjustment with respect to the vertical support frame.

9. The multi-position body support of claim 8 wherein the foot supports are each mounted to the vertical support frame for adjustment toward and away from the horizontal axis of rotation of the vertical support frame with respect to the base frame.

10. The multi-position body support of claim 6 wherein the foot supports are each mounted to the vertical support frame for lateral adjustment with respect to the vertical support frame.

11. The multi-position body support of claim 6 wherein the foot supports are mounted to the vertical support frame for adjustment toward and away from the horizontal axis of rotation of the vertical support frame with respect to the base frame.

12. The multi-position body support of claim 1 wherein the foot supports, are mounted on the vertical support frame for rotation about a horizontal axis.

13. The multi-position body support of claim 12 wherein the foot supports are each mounted to the vertical support frame for rotation about a vertical axis.

14. The multi-position body support of claim 13 wherein the foot supports are mounted to the vertical support frame for lateral adjustment with respect to the vertical support frame.

15. The multi-position body support of claim 1 wherein the body supports further comprise foot supports mounted to the vertical support frame for rotation about a vertical axis.

16. The multi-position body support of claim 1 wherein the body supports further comprise a pair of foot supports, each mounted on the vertical support frame for lateral adjustment with respect to the vertical support frame.

17. The multi-position body support of claim 1 wherein the base frame has caster wheels which are mounted for rotation about a vertical and a horizontal axis and locks for locking the rotational movement of the caster wheel about a vertical axis and locking the rotation of the wheels about a horizontal axis.

18. The multi-position body support of claim 1 wherein the vertical support frame comprises at least one vertical support tube and a knee support frame having at least one tube which is slidably received on the at least one vertical support tube and a fastener for securing the knee support frame on the vertical support tube in an adjusted position.

19. The multi-position body support of claim 18 wherein the vertical support frame further comprises a height adjustment frame including at least one tube which is slidably received on the at least one vertical support tube and a fastener for adjustably securing the height adjustment frame on the vertical support tube.

20. The multi-position body support of claim 1 wherein the vertical support frame further comprises at least one vertical support tube and a height adjustment frame including at least one tube which is slidably received on the at least one vertical support tube and a fastener for securing the height adjustment frame in one of multiple adjusted positions with respect to the vertical support tube.

21. The multi-position body support according to claim 1 wherein the brace is a lockable air cylinder for infinite adjustment between the first and second portions of the brace.

22. The multi-position body support according to claim 21 wherein the cylinder has an actuating pin to unlock the cylinder when depressed and further comprising a foot pedal movably mounted on the base frame for movement between neutral and actuating positions; and a coupling between the foot pedal and the actuating pin to unlock the cylinder when the foot pedal is moved between neutral and actuating positions.

23. The multi-position body supporting according to claim 1 wherein the first and second portions of the brace are biased with respect to each other to extend the brace and raise the vertical support frame to a vertical position.

24. The multi-position body support according to claim 1 wherein the body supports comprise a trunk support mounted at an upper portion of the vertical support frame and a hip support mounted beneath the body supports on the vertical support frame and the fasteners include straps which extend between said trunk supports and said hip supports.

25. A multi-position body support according to claim 24 wherein said body supports further comprise at least one trunk restraint pad mounted to the trunk support and adapted to restrain a front portion of a patient body in the supine and vertical positions, the at least one trunk support and said straps between said trunk supports and said hip supports being connected to form a harness for said patient in said supine and vertical positions.

26. In a multi-position body support comprising:

a base frame adapted to be supported by a floor;

an elongated vertical support frame which is pivotally mounted to the base frame for rotation about a horizontal axis;

body supports mounted to the vertical support frame for supporting a user on the vertical support frame, the body supports having fasteners for securing the user to the body supports; and an adjustable brace between the base frame and the vertical support frame to control the angular orientation of the vertical support frame with respect to the base frame;

the improvement which comprises:

the vertical support frame comprises a pair of parallel support tubes;

each of the body supports having a mounting plate adjacent to and on one side of the support tubes and further having a fastener receiver;

a clamping plate juxtaposed to each of the body supports in registry with one of the mounting plates in a respective body support on another side of the support tubes; and an adjustable fastener extending through the clamping plate and in adjustable engagement with the fastener receiver in the mounting plate, whereby the body supports are selectively clamped to the parallel support tubes for longitudinal movement with respect thereto.

27. In a multi-position body support comprising:

a base frame adapted to be supported by a floor;

an elongated vertical support frame which is pivotally mounted to the base frame for rotation about a horizontal axis;

body supports mounted to the vertical support frame for supporting a user on the vertical support frame, the body supports having fasteners for securing the user to the body supports; and an adjustable brace between the base frame and the vertical support frame to control the angular orientation of the vertical support frame with respect to the base frame;

the improvement which comprises:

the body supports comprise a pair of foot supports adapted to mount feet of a user supported by the multi-position body support, the foot supports being mounted to the vertical support frame for rotation about an axis perpendicular to the axis of rotation between the vertical support assembly and the base frame.

28. The multi-position body support of claim 21 wherein the foot supports are further mounted on the vertical support frame for rotation about a horizontal axis with respect thereto.

29. The multi-position body support according to claim 28 wherein the foot supports are each mounted on the vertical support frame for lateral adjustment with respect to the vertical support frame.

30. The multi-position body support according to claim 29 wherein the foot supports are each mounted on the vertical support frame for adjustment toward and away from the axis of rotation of the vertical support with respect to the base frame.

31. The multi-position body support according to claim 21 wherein the foot supports are each mounted on the vertical support assembly for adjustment toward and away from the axis of rotation of the vertical support frame with respect to the base frame.

32. In a multi-position body support comprising a base frame adapted to be supported by a floor;

an elongated vertical support frame which is pivotally mounted to the base frame for rotation about a horizontal axis;

body supports mounted to the vertical support frame for supporting a user on the vertical support frame, the body supports having fasteners for securing the user to the body supports; and an adjustable brace between the base frame and the vertical support frame to control the angular orientation of the vertical support frame with respect to the base frame;

the improvement which comprises:

the vertical support frame comprises at least one vertical support tube, a knee support frame having at least one tube which is slidably received on the at least one vertical support tube and a fastener for securing the knee support frame on the at least one vertical support robe in an adjusted position on the vertical support tube;

the vertical support frame further comprises a height adjustment frame including at least one extension tube which is slidably received on the at least one vertical support tube and a fastener for adjustably securing the height adjustment frame on the at least one vertical support tube in an adjusted position; and some of the body supports are slidably clamped to the knee support frame and other of the body supports are clamped to the height adjustment frame wherein said some body supports are moveable with respect to the knee support frame and the vertical support frame independent of the movement of the other body supports with respect to said vertical support frame.

33. The multi-position body support of claim 32 wherein the body supports comprise a trunk support which is mounted to the height adjustment frame.

34. The multi-position body support of claim 32 wherein the body supports comprise a head support mounted in a vertical orientation on the height adjustment frame for supporting the head of the user in the supine position.

35. In a multi-position body support comprising:

a base frame adapted to be supported by a floor;

an elongated vertical support frame which is pivotally mounted to the base frame for rotation about a horizontal axis;

body supports mounted to the vertical support frame for supporting a user on the vertical support frame, the body supports having fasteners for securing the user to the body supports;

an adjustable brace between the base frame and the vertical support frame and having a first and a second portion which are adjustable with respect to each other to lengthen or shorten the length of the brace to control the angular orientation of the vertical support frame with respect to the base frame;

the improvement which comprises:

the brace comprises an air cylinder and the first and second portions of the brace are biased with respect to each other by air pressure in the air cylinder so as to extend the brace to raise the vertical support frame into a vertical position; and the adjustable brace is pivotally mounted to the base frame for rotation about a horizontal axis, which is parallel to and spaced a fixed distance from the horizontal axis of the vertical support frame.

36. The multi-position body support according to claim 35 and further comprising a releasable lock between the first and second portions of the brace for releasably locking the first and second portions of the brace in adjusted positions with respect to each other;

a foot pedal movably mounted on the base frame for movement between neutral and actuating positions; and a coupling between the foot pedal and the lock for releasing the lock between the first and second positions of the brace when the foot pedal is moved between neutral and actuating positions;

whereby the vertical support frame can be easily adjusted with respect to the base frame by moving the foot pedal between the neutral and actuating positions and adjusting the position of the vertical support frame with respect to the base frame.

37. The multi-position body support according to claim 36 wherein the brace comprises a gas cylinder.

38. The multi-position body support of claim 2 wherein the body supports further comprise a pair of knee supports, each of which is mounted on a vertical support frame for rotation about a horizontal axis.

39. The multi-position body support of claim 38 wherein the knee supports are mounted to the pair of parallel support tubes for longitudinal adjustment of the knee supports with respect to the parallel support tubes.

40. The multi-position body support of claim 39 wherein the knee supports are mounted to the pair of parallel support tubes for lateral adjustment with respect to the pair of parallel support tubes.

41. The multi-position body support of claim 40 wherein the knee supports comprise a U-shaped structural foam member having a belt spanning the ends of the legs of the U-shaped foam member.

42. The multi-position body support of claim 39 wherein the knee supports comprise a U-shaped structural foam member having a belt spanning the ends of the legs of the U-shaped foam member.

43. The multi-position body support of claim 39 wherein the body supports further comprise a hip support mounted to the vertical support frame for longitudinal adjustment with respect to the parallel support tubes.

44. The multi-position body support of claim 43 wherein the hip support comprises a U-shaped structural foam member having a belt spanning the ends of the legs of the U-shaped foam member.

45. The multi-position body support of claim 16 wherein the body supports further comprises a trunk support mounted to the vertical support frame for longitudinal adjustment with respect to the parallel support tubes.

46. The multi-position body support of claim 45 wherein the trunk support has a back portion and side portions, the back portion is larger than the side portions and the side portions are tapered for an ergonomic fit under the arms of the user.

47. The multi-position body support of claim 46 wherein the trunk support comprises a U-shaped structural foam member having a belt spanning the ends of the legs of the U-shaped foam member.

48. In a multi-position body support comprising:

a base frame adapted to be supported by a floor;

an elongated vertical support frame which is pivotally mounted to the base frame for rotation about a horizontal axis;

body supports mounted to the vertical support frame for supporting a user on the vertical support frame for supporting a user on the vertical support frame, the body supports having fasteners for securing the user to the body support;

an adjustable brace between the base frame and the vertical support frame having a first and a second portion which are adjustable with respect to each other to lengthen or shorten the length of the brace to control the angular orientation of the vertical support frame with respect to the base frame, and the improvement which comprises:

the brace comprises a lockable air cylinder positioned on the base frame and on the vertical support frame so that the brace adjustably supports the vertical support frame for infinite adjustment between a substantially horizontal position and a vertical position with respect to the base frame, the cylinder has an actuating pin to unlock the cylinder when depressed; and further comprising a foot pedal movably mounted on the base frame with movement between neutral and actuating positions; and a coupling between the foot pedal and the actuating pin to unlock the cylinder when the foot pedal is moved between neutral and actuating positions.

49. The multi-position body support according to claim 48 wherein the cylinder biases the brace in an extended position.

50. In a multi-position body support comprising:

a base frame adapted to be supported by a floor;

an elongated vertical support frame which is pivotally mounted to the base frame for rotation about a horizontal axis;

body supports mounted to the vertical support frame for supporting a user on the vertical support frame, the body supports having fasteners for securing the user to the body supports, the body supports including a trunk support mounted on an upper portion of the vertical support frame and a hip support mounted beneath the body supports on the vertical support frame and the fasteners include straps which extend between the trunk support and the hip support;

at least one trunk restraint pad mounted to the trunk support and adapted to restrain a front portion of a user's body in the supine and vertical positions, the at least one trunk support and said straps between said trunk supports and said hip supports being connected to form a harness for said patient and said supine and vertical positions; and an adjustable brace between the base frame and the vertical support frame having a first and a second portion which are adjustable with respect to each other to lengthen or shorten the length of the brace to control the angular orientation of the vertical support frame with respect to the base frame, and the brace is positioned on the base frame and on the vertical support frame so that the brace adjustably supports the vertical support frame between a substantially horizontal position and a substantially vertical position with respect to the base frame.

* * * * *

UNITED STATES PATENT AND TRADEMARK OFFICE

CERTIFICATE OF CORRECTION

PATENT NO. : 5,489,258

DATED : February 6, 1996

INVENTOR(S) : Wohnsen et al.

It is certified that error appears in the above-indentified patent and that said Letters Patent is hereby corrected as shown below:

Claim 28, column 16, line 10, "21" should read --27--.

Claim 31, column 16, line 23, "21" should read --27--.

Signed and Sealed this

Twentieth Day of August, 1996

Attest:

BRUCE LEHMAN

*Attesting Officer* *Commissioner of Patents and Trademarks*

UNITED STATES PATENT AND TRADEMARK OFFICE

CERTIFICATE OF CORRECTION

PATENT NO. : 5,489,258

DATED : February 6, 1996

INVENTOR(S) : Wohnsen et al.

It is certified that error appears in the above-indentified patent and that said Letters Patent is hereby corrected as shown below:

Claim 48, column 18, lines 26 and 27 "for supporting a user on the vertical support frame" should be deleted (it was duplicated).

Signed and Sealed this

Eighth Day of October, 1996

*Attest:*

BRUCE LEHMAN

*Attesting Officer*

*Commissioner of Patents and Trademarks*